(12) United States Patent
Hwang et al.

(10) Patent No.: US 7,687,629 B2
(45) Date of Patent: Mar. 30, 2010

(54) PROCESS FOR PREPARING 4-AMINOMETHYL-3-ALKOXYIMINOPYRROLIDINE METHANESULFONATE

(75) Inventors: Gyo-Hyun Hwang, Daejeon (KR); Yeong-Dae Kim, Daejeon (KR); Hyun Nam, Seoul (KR); Jay-Hyok Chang, Daejeon (KR); Hyun-Ik Shin, Daejeon (KR); Young-Keun Kim, Daejeon (KR); Kyung Hee Lee, Kyongsangbuk-do (KR); Jae Sung Lee, Kyongsangbuk-do (KR); Hyun-Kuk Noh, Seoul (KR)

(73) Assignee: LG Life Sciences Ltd. (KR)

( * ) Notice: Subject to any disclaimer, the term of this patent is extended or adjusted under 35 U.S.C. 154(b) by 66 days.

(21) Appl. No.: 11/882,929

(22) Filed: Aug. 7, 2007

(65) Prior Publication Data

US 2007/0282107 A1 Dec. 6, 2007

Related U.S. Application Data

(62) Division of application No. 10/548,324, filed as application No. PCT/KR2004/000476 on Mar. 6, 2004, now Pat. No. 7,271,272.

(30) Foreign Application Priority Data

Mar. 7, 2003 (KR) ................ 10-2003-0014469

(51) Int. Cl.
*C07D 471/02* (2006.01)
(52) U.S. Cl. ............... 546/123; 546/112; 546/113; 546/122
(58) Field of Classification Search ........... 546/112, 546/113, 122, 123
See application file for complete search history.

(56) References Cited

U.S. PATENT DOCUMENTS

| 3,562,287 | A | | 2/1971 | Gadekar et al. |
| 5,633,262 | A | | 5/1997 | Hong et al. |
| 5,776,944 | A | * | 7/1998 | Hong et al. ............... 514/300 |
| 5,869,670 | A | | 2/1999 | Hong et al. |
| 6,307,059 | B1 | * | 10/2001 | Chang et al. ............... 548/531 |
| 6,703,512 | B1 | * | 3/2004 | Grinter et al. ............... 548/557 |
| 6,803,467 | B2 | * | 10/2004 | Grinter et al. ............... 546/156 |
| 7,199,242 | B2 | * | 4/2007 | Brechtelsbauer et al. ..... 546/123 |
| 7,232,907 | B2 | * | 6/2007 | Hayler et al. ............... 546/123 |
| 7,271,272 | B2 | * | 9/2007 | Hwang et al. ............... 548/557 |

FOREIGN PATENT DOCUMENTS

| EP | 0 688 772 B1 | 5/1999 |
| WO | WO 99/07696 A1 | 2/1999 |
| WO | WO 99/44991 A1 | 9/1999 |
| WO | WO 01/17961 A2 | 3/2001 |
| WO | WO 01/68649 A1 | 9/2001 |
| WO | WO 02/18336 A1 | 3/2002 |
| WO | WO 03/011450 A1 | 2/2003 |

OTHER PUBLICATIONS

Gadekar et al., "Syntheses and Hypotensive Activities of 3-Amino-4H-pyrrolo[3,4-c]isoxaxoles and Derivatives," Journal of Medicinal Chemistry, 1968, 11:3:453-456.
Nishimura et al., "Contact Hydrogenation Reaction - Application to Organic Synthesis," TokyoKagakuDohjin, 1987, pp. 199-201.

* cited by examiner

*Primary Examiner*—Golam M Shameem
(74) *Attorney, Agent, or Firm*—Finnegan, Henderson, Farabow, Garrett & Dunner, LLP

(57) ABSTRACT

The present invention relates to a process for the preparation of 4-aminomethyl-3-alkoxyiminopyrrolidine methanesulfonate, a key intermediate of quinolone antibiotics. According to the process of the present invention, the total number of steps has been shortened to 2-3 steps, the solid separation is not required, and the use of costly chemicals, particularly $(BOC)_2O$ (t-butoxycarbonyl anhydride), several organic solvents and reactants, is eliminated.

10 Claims, No Drawings

PROCESS FOR PREPARING 4-AMINOMETHYL-3-ALKOXYIMINOPYRROLIDINE METHANESULFONATE

This application is a divisional of application Ser. No. 10/548,324 filed Sep. 7, 2005 now U.S. Pat. No. 7,271,272, which is the National Stage of International Application No. PCT/KR2004/000476, filed Mar. 6, 2004, which claims benefit under 35 U.S.C. 119 of Republic of Korea Application No. 10-2003-0014469, filed Mar. 7, 2003, all of which are incorporated by reference.

TECHNICAL FIELD

The present invention relates to a process for preparing 4-aminomethyl-3-alkoxyiminopyrrolidine methanesulfonate of the following formula (I):

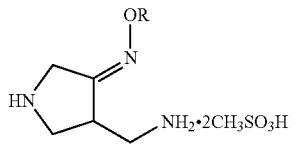

wherein R represents $C_{1-4}$ alkyl or $C_{1-4}$ haloalkyl, which is a useful intermediate for preparing quinolone antibiotics, particularly (R,S)-7-(3-aminomethyl-4-syn-alkoxyimino-pyrrolidin-1-yl)-1-cyclopropyl-6-fluoro-4-oxo-1,4-dihydro-1,8-naphthyridine-3-carboxylic acid of the following formula (VI):

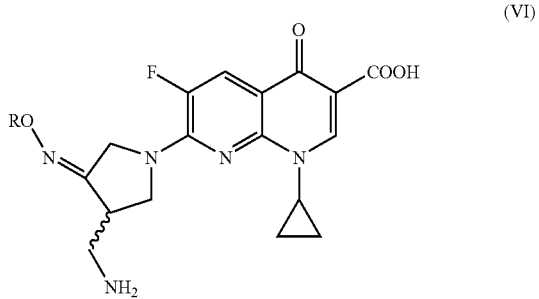

wherein R is as defined above, salt, or hydrate thereof as described in U.S. Pat. No. 5,633,262 and EP 0 688 772 A1.

The process of the present invention adopts a new synthetic pathway having shortened number of steps for preparing Compound (I) compared with the earlier processes, whereby Compound (I) is produced in a high yield. Accordingly, the present invention cuts the production cost down, and ultimately contributes to economic preparation of Compound (VI).

BACKGROUND ART

WO99/44991 and WO01/17961 disclose a process for preparing Compound (I) as depicted in Reaction Scheme 1:

Reaction Scheme 1

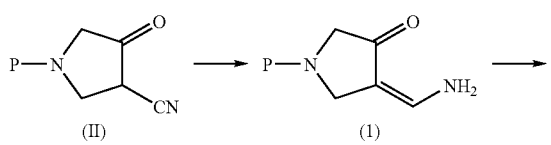

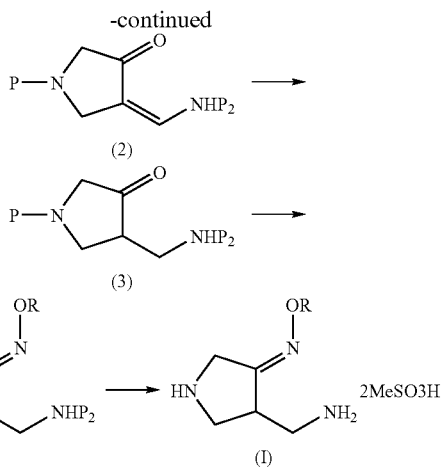

wherein R represents $C_{1-4}$ alkyl or $C_{1-4}$ haloalkyl, and P and $P_2$ each represent the same or different protecting group.

WO99/44991 specifically describes a process from Compound (II) to Compound (3) in the above Reaction Scheme 1, which consists of two reduction steps of the nitrile group and one protection step of the amine group.

Compound (1) is produced from Compound (II) by a hydrogenation process using such a catalyst as Ra—Ni, etc. for the first reduction of nitrile group. As the solvent, a mixture of water and isopropyl alcohol is used in an amount of 2 to 20 equiv with respect to Compound (II).

Compound (2) is produced from Compound (1) by protecting the amine group. As the protecting group, formyl, acetyl, trifluoroacetyl, benzoyl, p-toluenesulfonyl, methoxycarbonyl, ethoxycarbonyl, t-butoxycarbonyl, benzyloxycarbonyl, p-methoxy-benzyl, trityl, tetrahydropyranyl, pivaloyl, etc. may be used. Among these protecting groups, t-butoxycarbonyl is particularly preferred. However, $(BOC)_2O$ used for the introduction of the t-butoxycarbonyl group is an expensive reagent to contribute about ⅓ of the total cost for preparing Compound (2) from Compound (1). Furthermore, the reaction temperature is difficult to control due to high exothermic and fast reaction rate. Failure of the control of the reaction temperature led to the formation of the dimer of Compound (2). Also, Compound (2) should be separated through an extractive work-up and solidification process. These work-up processes make this process complicate.

Compound (3) is produced from Compound (2) by the second hydrogenation process using Pd/C catalyst. The catalyst is used in an amount of 0.5-20% by weight, and an amine or buffer solution is used to prevent reduction of the carbonyl group at 3-position of the pyrrolidine ring.

The process for preparing Compound (I) from Compound (4) is disclosed in WO001/17961, wherein the protecting group is removed using methanesulfonic acid to form a salt. However, this process requires two recrystallization processes to produce high quality product. These operations lowered the productivity and resulted in low yield.

Differently from the Reaction Scheme 1 above, EP 0 688 772 A1 describes a process for preparing Compound (4) from Compound (II) as depicted in Reaction Scheme 2.

Reaction Scheme 2

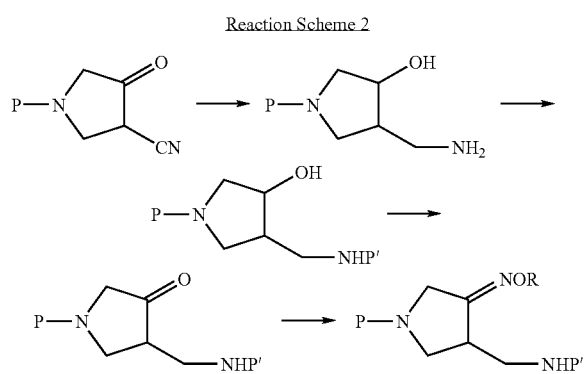

wherein R represents $C_{1-4}$ alkyl or $C_{1-4}$ haloalkyl, and P and P' each represent the same or different protecting group.

EP 0 688 772 A1 provides a process for preparing Compound (4) from Compound (II) wherein the carbonyl and nitrile groups are reduced simultaneously to give the amino alcohol intermediate, and the alcohol group is selectively oxidized to give the carbonyl group again. This process requires reagents difficult to be applied to the industrial production, and so has little merit compared with the process of WO99/44991. Particularly, this process uses a homogeneous catalyst for the hydrogenation of the nitrile group, but preparation of the homogeneous catalyst and its recovery and reproduction after the reaction are not easy.

DISCLOSURE

As mentioned above, the earlier processes for preparing Compound (I) have such problems as complicated process, high production cost, poor reproducibility, etc., and so it has been required to develop an improved new process.

Extensive study led to the present invention wherein the two step hydrogenation of WO99/44991 is converted into one step hydrogenation, and the use of expensive organic reagents, particularly (BOC)$_2$O, and various organic solvents and reagents is avoided.

Therefore, the present invention provides a new and effective process for preparing Compound (I).

The present invention also provides a process for preparing Compound (VI) by using Compound (I) prepared by the above process.

The present invention also provides new intermediates used in the process for preparing Compound (I).

BEST MODE FOR CARRYING OUT THE INVENTION

As the first aspect, the present invention provides a process for preparing Compound (I):

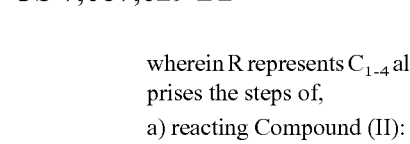

wherein R represents $C_{1-4}$ alkyl or $C_{1-4}$ haloalkyl, which comprises the steps of, a) reacting Compound (II):

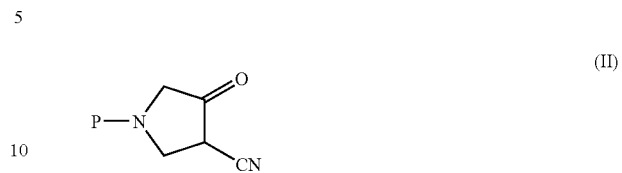

wherein P represents a protecting group, with alkoxyamine or haloalkoxyamine or salt thereof in the presence of a base to give Compound (III):

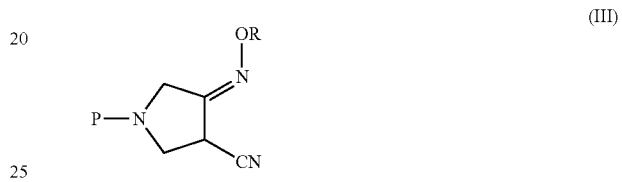

wherein R and P each are as defined above, b) reacting Compound (III) with methanesulfonic acid to give Compound (IV):

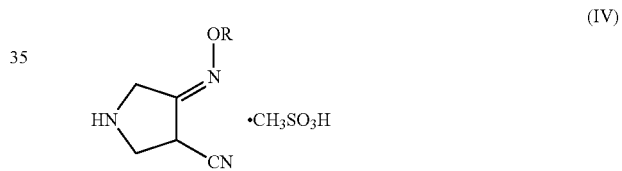

wherein R is as defined above, and c) adding methanesulfonic acid and hydrogenation catalyst to Compound (IV) and subjecting the compound to hydrogenation reaction to give Compound (I).

In the above process, the protecting group P may include formyl, acetyl, trifluoroacetyl, benzoyl, p-toluenesulfonyl, methoxycarbonyl, ethoxycarbonyl, t-butoxycarbonyl, benzyloxycarbonyl, p-methoxybenzyl, trityl, tetrahydropyranyl, pivaloyl, etc., and the most preferable one is t-butoxycarbonyl (BOC). Also, R is preferably methyl.

The above process for preparing Compound (I) may be depicted as follows:

Reaction Scheme 3

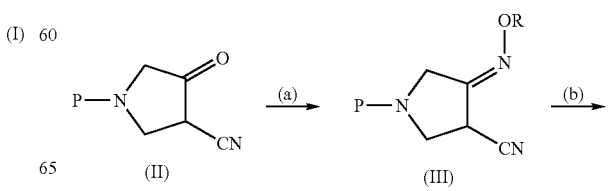

-continued $$\text{(IV)} \quad \underset{\text{HN}}{\overset{\text{OR}}{\underset{\text{CN}}{\bigvee}}} \cdot CH_3SO_3H \xrightarrow{(c)} \underset{\text{HN}}{\overset{\text{OR}}{\underset{\text{NH}_2 \cdot 2CH_3SO_3H}{\bigvee}}} \text{(I)}$$

wherein R represents $C_{1-4}$ alkyl or $C_{1-4}$ haloalkyl, and P represents a protecting group.

Step (a)

The process for converting Compound (II) into Compound (III) is carried out in the presence of a base. A preferably used base includes triethylamine, tri-n-butylamine, diisopropylethylamine, pyridine, 4-dimethylaminopyridine, 4-(4-methyl-piperidin-1-yl)-pyridine, and sodium acetate. The base is preferably used in an amount of 0.01~10 equiv with respect to Compound (II).

The reactant, alkoxyamine or haloalkoxyamine, is preferably used in the form of an acid addition salt, particularly hydrochloride form. The alkoxyamine, haloalkoxyamine, or salt thereof is used in an amount of 1 to 2 equiv with respect to Compound (II).

Solvents, which can be used in this step include water, organic solvent, or a mixture thereof, preferably straight-chain or branched $C_{1-6}$-alcohol, preferably MeOH, EtOH, or IPA (isopropyl alcohol).

The reaction temperature and time in step (a) may be varied depending on the base and solvent used. The reaction temperature ranges, for example, from room temperature to 200° C. But, a person skilled in the art may easily determine the appropriate reaction temperature and time according to the base and solvent used.

One best mode of the present invention is to use triethylamine as the base. In this case, Compound (II) is refluxed with alkoxyamine hydrochloride in the presence of triethylamine and methanol for 22 hours.

Another best mode of the present invention is to use sodium acetate as the base. In this case, Compound (II) is added to a solution of alkoxyamine hydrochloride and sodium acetate in ethanol or methanol, and the mixture is refluxed for about 18 hours.

Another best mode of the present invention is to use pyridine as the base. In this case, Compound (II) is added to a solution of alkoxyamine hydrochloride and pyridine in isopropyl alcohol or methanol, and the mixture is reacted with stirring for about 5 hours. This process is convenient because it is carried out at room temperature.

The pure Compound (III) may be obtained by applying the processes exemplified in the above best modes without any side product that is detected by HPLC.

Step (b)

The reaction from Compound (III) to Compound (IV) is to remove the protecting group by methanesulfonic acid. Methanesulfonic acid is used in an amount of about 0.5 to 3 equiv, preferably about 1 to 1.2 equiv with respect to Compound (III). The protecting group is easily removed by such an acid as methanesulfonic acid. As shown in the examples below, it can be identified by NMR, HPLC, etc. that the protecting group is easily removed by about 30 minutes' reflux.

Step (c)

The reaction from Compound (IV) to the desired compound, Compound (I), is a selective hydrogenation reaction using such Raney type metal catalysts as Raney-Ni, Raney-Co, etc. or metal catalysts incorporated into supports such as activated carbon, alumina, silica, etc. Metals used as the active site of the catalyst include the metals like Ni, Co, Pt, Pd, Ru, Rh, Ir, Cu, etc. and the palladium precursors like palladium chloride, palladium nitrate, palladium acetate, etc., but the palladium catalyst is more preferable. Usually, activity of the catalyst may be changed by the influence of other metals added in a small amount in the form of a co-catalyst, or by reaction conditions such as pressure, temperature, etc., and so the selectivity for the desired product can be controlled thereby. The hydrogenation catalyst particularly preferable for being used in the present invention is Pd catalyst not only having 1 to 20% by weight of Pd but also incorporated in a support selected from the group consisting of carbon, silica, and alumina. This hydrogenation catalyst is preferably used in an amount of 0.01 to 10% by weight with respect to Compound (IV) based on the metal component.

The hydrogenation reaction is carried out preferably under the temperature range of 0 to 50° C. and the hydrogen pressure of 1 to 100 atm.

Methanesulfonic acid is added to the reaction solution in an amount of about 0.5 to 3 equiv, preferably about 1 to 1.2 equiv with respect to Compound (III).

As the solvent used in this step, one or more organic solvents selected from the group consisting of methanol, ethanol, n-propanol, isopropanol, tetrahydrofuran, dimethoxyethane, dioxane, ethyl acetate and dichloromethane, preferably methanol can be mentioned.

The step (c) reaction may also be carried out in the presence of an acid as a further additive. The acid includes hydrochloric acid, nitric acid, sulfuric acid, acetic acid, methanesulfonic acid, etc., and methanesulfonic acid is the most preferable. In order to increase the yield, it is preferable to add the acid in an amount to control the reaction solution to pH 1 to 2.5 during the hydrogenation reaction, and the acid may be added to the reaction solution at the time of initiation, or continuously in the middle, of the reaction.

As the second aspect, the present invention provides a process for preparing Compound (I):

$$\underset{\text{HN}}{\overset{\text{OR}}{\underset{\text{NH}_2 \cdot 2CH_3SO_3H}{\bigvee}}} \quad \text{(I)}$$

wherein R represents $C_{1-4}$ alkyl or $C_{1-4}$ haloalkyl, which comprises the steps of, a) reacting Compound (II):

$$\underset{P-N}{\overset{O}{\underset{CN}{\bigvee}}} \quad \text{(II)}$$

wherein P represents a protecting group, with alkoxyamine or haloalkoxyamine or salt thereof in the presence of a base to give Compound (III):

$$\underset{P-N}{\overset{OR}{\underset{CN}{\bigvee}}} \quad \text{(III)}$$

wherein R and P each are as defined above, and b) adding methanesulfonic acid and hydrogenation catalyst to Compound (III) and subjecting the compound to hydrogenation reaction to give Compound (I).

In the above process, R is preferably methyl and P is preferably t-butoxycarbonyl (BOC).

The above process for preparing Compound (I) may be depicted as follows:

Reaction Scheme 4

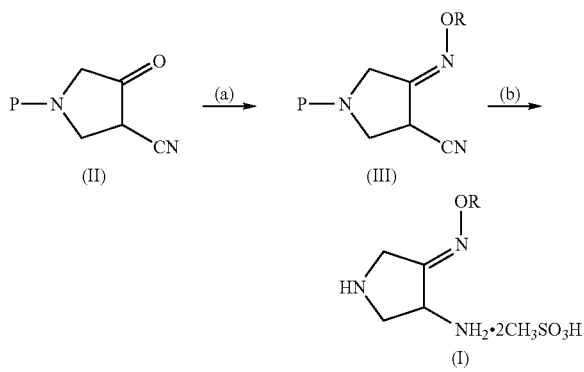

wherein R represents $C_{1-4}$ alkyl or $C_{1-4}$ haloalkyl, and P represents a protecting group.

This second process has such merits as explained for the first process, and is more effective since the number of steps is decreased from 3 to 2.

Step (a)

Step (a) of the second process is carried out according to the same manner as Step (a) of the first process.

Step (b)

In Step (b) of the second process, Steps (b) and (c) of the first process are concurrently carried out.

The amount of methanesulfonic acid is the total amount of methanesulfonic acid used in Steps (b) and (c) of the first process, i.e., about 1 to 6 equiv, preferably about 1.5 to 2.5 equiv with respect to Compound (III). Further, the hydrogenation catalyst is introduced in an amount of 0.01 to 10% by weight with respect to Compound (III) based on the metal component.

The solvent used in Step (b) of the second process is an organic solvent selected from the group consisting of methanol, ethanol, n-propanol, isopropanol, tetrahydrofuran, dimethoxyethane, dioxane, ethyl acetate and dichloromethane, or a mixture of this organic solvent and water. The mixture of an organic solvent and water is more preferable. When the mixture is used, the mixing ratio is between 0.2 to 50 volumes of the organic solvent to 1 volume of water. Particularly preferable solvent is a mixture of methanol and water.

Besides, the same reaction conditions as Step (c) of the first process may be applied to this step.

As the third aspect, the present invention provides a process for preparing Compound (VI):

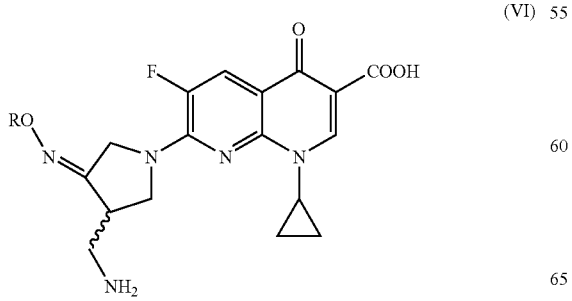

wherein R represents $C_{1-4}$ alkyl or $C_{1-4}$ haloalkyl, salt or hydrate thereof, which comprises the step of reacting Compound (I):

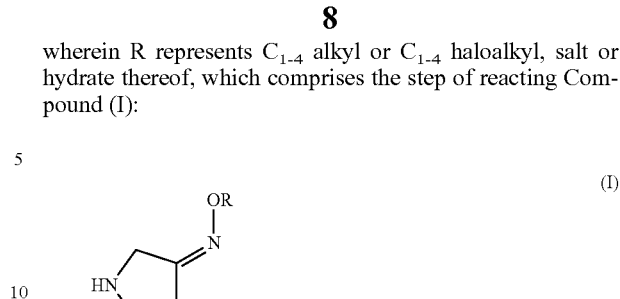

wherein R is as defined above, which is prepared according to the first or second process as explained above, with Compound (V):

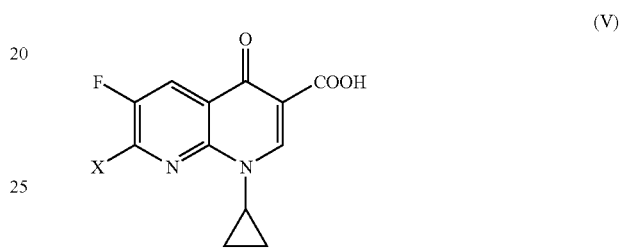

wherein X represents a leaving group, preferably halogen.

In this process, the reaction of Compound (I) with Compound (V) is preferably carried out in the presence of a base and in a solvent. The specific reaction conditions may be easily controlled by a person skilled in the art by referring to PCT/GB00/03358.

Compound (VI) is preferably (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate or its hydrate.

As the fourth aspect, the present invention provides new Compound (III) with the following formula:

wherein R represents $C_{1-4}$ alkyl or $C_{1-4}$ haloalkyl, and P represents a protecting group.

P is preferably t-butoxycarbonyl (BOC).

As the fifth aspect, the present invention also provides new Compound (IV) with the following formula:

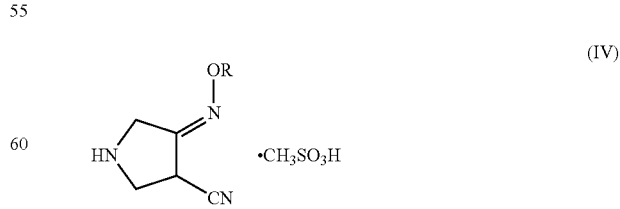

wherein R represents $C_{1-4}$ alkyl or $C_{1-4}$ haloalkyl.

Compounds (III) and (IV) above are useful as intermediates for preparing Compound (I).

The present invention will be more specifically explained by the following examples. However, it should be understood that they do not intend to limit the present invention in any manner.

EXAMPLE 1

(1) Synthesis of Compound (III)

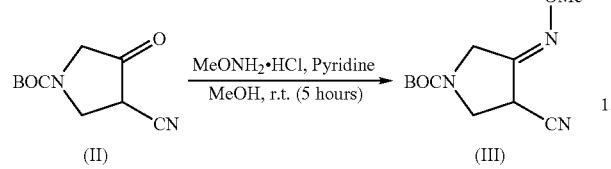

To a stirred solution of Compound (II) (10.5 g, 0.05 mol) in 100 ml of methanol in the presence of pyridine (4.84 ml, 1.2 equiv) was added methoxylamine hydrochloride (5.0 g, 1.2 equiv) at room temperature. After 5 hours, the completion of reaction was confirmed by HPLC under the following conditions:

Column: Capcellpak C18
Solvent: AN/H$_2$O/TFA=60/40/0.1
Wavelength: 210 nm
Flow rate: 1 ml/min
Temperature: room temp.

The volatiles were thoroughly removed under vacuum, and ethyl acetate (50 ml) was added to the residue. The organic layer was washed twice with saturated aqueous NaHCO$_3$ solution (100 ml) and twice with brine (100 ml). Anhydrous magnesium sulfate was added to the organic layer to remove the moisture, and the mixture was concentrated under vacuum to give Compound (III) (11.09 g, Yield 92.8%).

$^1$H NMR (400 MHz, CDCl$_3$) δ (ppm): 1.47 (s, 9H), 3.69 (dd, 1H), 3.95 (s, 3H), 3.98~4.06 (m, 2H), 4.10~4.22 (m, 2H)

(2) Synthesis of Compound (IV)

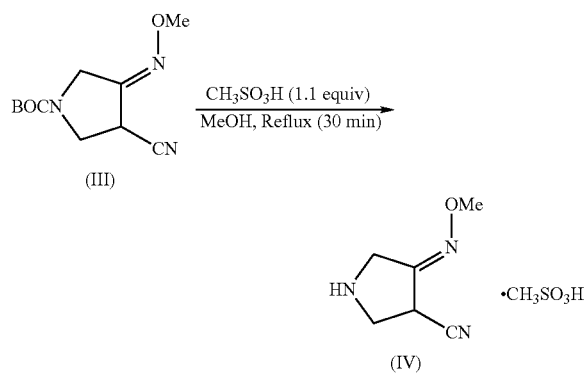

To a stirred solution of Compound (III) (3.0 g, 0.0125 mol) in 25 ml of methanol was added dropwise methanesulfonic acid (0.91 ml, 1.1 equiv, 98%) and the mixture was heated at reflux for 30 minutes. The reaction mixture was cooled to room temperature. The mixture was concentrated under reduced pressure and recrystallized to give Compound (IV) (4.14 g, Yield 98.8%).

$^1$H NMR (400 MHz, D$_2$O) δ (ppm): 2.69 (s, 3H), 3.76~3.82 (dd, 1H), 3.88 (s, 3H), 3.92~3.98 (m, 2H), 4.03~4.21 (dd, 2H)

(3) Synthesis of Compound (I)

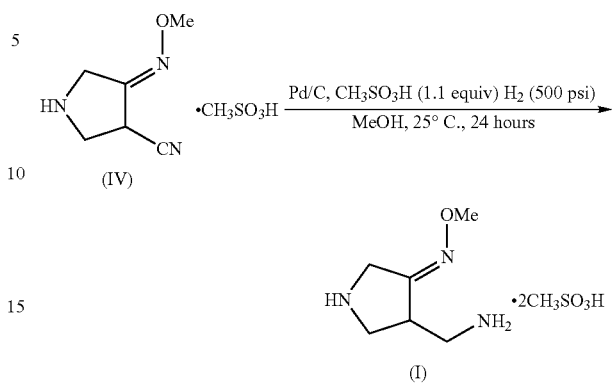

To a stirred solution of Compound (IV) (4.19 g, 0.0125 mol) in 80 ml of methanol were added Pd/C (0.3 g, wet basis) as a catalyst and methanesulfonic acid (1.0 ml, 1.1 equiv, 98%), and hydrogenation reaction was carried out for 24 hours under the reaction temperature of 25° C. and hydrogen pressure of 500 psig. After the reaction was completed, the mixture was passed through a celite to remove the catalyst, and the filtrate was concentrated under vacuum. Methanol (50 ml) was added to the residue, and Compound (I) (1 mg) was added as a seed. The mixture was stirred at room temperature for 1 hour and filtered. The resulting solid was dissolved in a water bath of about 50° C., recrystallized at −20° C., and filtered to give Compound (I) (0.99 g, Yield 23.1%).

$^1$H NMR (400 MHz, DMSO) δ (ppm): 2.39 (s, 6H), 3.07 (dd, 1H), 3.16 (dd, 1H), 3.24~3.30 (m, 2H), 3.66~3.73 (m, 1H), 3.87 (s, 3H), 3.97 (dd, 2H)

EXAMPLE 2

(1) Synthesis of Compound (III)

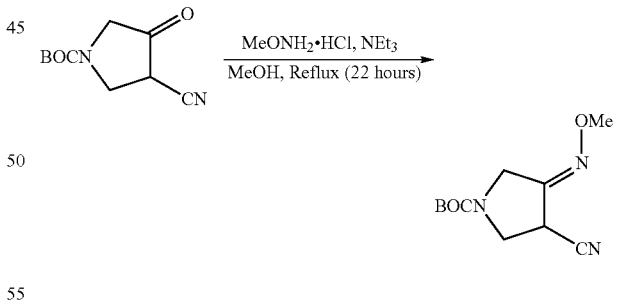

To a stirred suspension of Compound (II) (10.5 g, 0.05 mol) in 100 ml of methanol were added methoxylamine hydrochloride (5.0 g, 1.2 equiv) and triethylamine (8.4 ml, 1.2 equiv) and the mixture was heated at reflux for 22 hours. The reaction mixture was cooled to room temperature. The mixture was concentrated under vacuum, and ethyl acetate (50 ml) was added to the residue. The organic layer was washed twice with saturated aqueous NaHCO$_3$ solution (100 ml) and twice with brine (100 ml). Anhydrous magnesium sulfate was added, filtered, and the filtrate was concentrated under vacuum to give Compound (III) (11.35 g, Yield 95.0%).

(2) Synthesis of Compound (IV)
Compound (IV) was prepared according to the same procedure as Example 1 (2).

(3) Synthesis of Compound (I)

Compound (I) was prepared according to the same procedure as Example 1 (3).

EXAMPLE 3

(1) Synthesis of Compound (III)

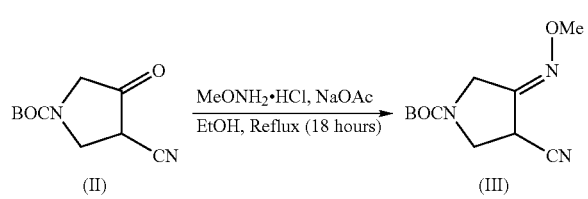

To a stirred suspension of Compound (II) (10.5 g, 0.05 mol) in 100 ml of methanol were added methoxylamine hydrochloride (5.0 g, 1.2 equiv) and sodium acetate (4.92 g, 1.2 equiv) and the mixture was heated at reflux for 18 hours. The reaction mixture was cooled to room temperature. The mixture was concentrated under vacuum and ethyl acetate (50 ml) was added to the residue. The organic layer was washed twice with saturated aqueous $NaHCO_3$ solution (100 ml) and twice with brine (100 ml). Anhydrous magnesium sulfate was added, filtered, and the filtrate was concentrated under vacuum to give Compound (III) (11.35 g, Yield 95.0%).

(2) Synthesis of Compound (IV)
Compound (IV) was prepared according to the same procedure as Example 1 (2).

(3) Synthesis of Compound (I)
Compound (I) was prepared according to the same procedure as Example 1 (3).

EXAMPLE 4

(1) Synthesis of Compound (III)
Compound (III) was prepared according to the same procedure as Example 1(1).

(2) Synthesis of Compound (IV)
Compound (IV) was prepared according to the same procedure as Example 1 (2).

(3) Synthesis of Compound (I)
Compound (I) (0.72 g, Yield 16.8%) was prepared according to the same procedure as Example 1 (3) except that the pressure in the hydrogenation reaction was lowered from 500 psig to 200 psig.

EXAMPLE 5

(1) Synthesis of Compound (III)
Compound (III) was prepared according to the same procedure as Example 1 (1).

(2) Synthesis of Compound (I)
To a 100 ml pressure reactor were added Compound (III) (5 g), methanol (40 ml) and water (10 ml). To this solution were added 10% Pd/C (0.18 g) and methanesulfonic acid (2.2 ml). The mixture was agitated at 30° C. under 100 psig of hydrogen for 1 hour. The catalyst was filtered out, and the filtrate was concentrated completely under reduced pressure. The residue was dissolved in methanol (10 ml) and Compound (I) (1 mg) was added as a seed at 5° C. to form crystal. The resulting crystal was cooled to −10° C. and filtered to give 3-aminomethyl-4-Z-methyloxyiminopyrrolidine methanesulfonate (3.15 g, Yield 45%).

EXAMPLE 6

Synthesis of (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid Triethylamine (5.1 ml) was added to 7-chloro-1-cyclopropyl-6-fluoro-4-oxo-1,4-dihydro-1,8-naphthyridine-3-carboxylic acid (3.05 g) in water (25 ml) at 15-20° C., and the mixture was stirred for 20 minutes. Compound (I) (3.86 g) prepared in Example 1 and water (5 ml) were added, and this mixture was stirred at 20-25° C. for 18 hours. The product thus obtained was filtered, and the filter cake was washed with water (30 ml) and ethanol (30 ml). Drying at 50° C. under vacuum gave the title compound (4.23 g) as a white solid. The identification data were the same as those of the authentic sample.

EXAMPLE 7

Synthesis of (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methane-sulfonate A solution of methanesulfonic acid (0.33 g, 3.43 mmol) in dichloromethane (1 ml) was added to a suspension of (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid (1.5 g at a purity of 89.9%, 3.46 mmol) in a mixture of dichloromethane (23.2 ml) and ethanol (2.7 ml) at 30° C. This mixture was stirred at 30° C. for 3 hours, and then cooled to 20° C. and filtered. The filter cake was washed with dichloromethane (20 ml) and dried at 50° C. under vacuum to give the title compound (1.71 g). The identification data were the same as those of the authentic sample.

EXAMPLE 8

Synthesis of (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate sesquihydrate (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate (27.5 g at a purity of 91%, 51.4 mmol) was stirred in a mixture of isopropanol (150 ml) and water (75 ml) and then heated to become a clear solution (52° C.). This solution was cooled to 34° C., and (R,S)-7-(3-aminomnethyl-4-syn-methoxyimino-pyrrolidin-1-yl)-1-cyclopropyl-6-fluoro-4-oxo-1,4-dihydro-1,8-naphthyridine-3-carboxylic acid methanesulfonate sesquihydrate was added thereto as a seed crystal. Thus obtained suspension was allowed to stand over 1 hour to 25° C. and then stirred for 18 hours. The slurry was cooled to 0-4° C., stirred for 2 hours, and filtered. The filter cake was washed with isopropanol (30 ml). The product was dried by suction for 2 hours, and further dried under vacuum at 50° C. The dried product was humidified by wet nitrogen to give the title sesquihydrate (22.9 g, 92%). The identification data were the same as those of the authentic sample.

EXPERIMENT 1

In order to determine whether Compound (I) prepared according to the present invention can be used as a material for antibiotics, Compound (I) prepared in Example 1 was analyzed by HPLC under the following conditions:

Column: Shodex ODP-50 6E (4.6×250 mm, 5 μm, Asahipak)
Solvent: AN/H$_2$O (including 5 mM 1-hexanesulfonic acid)/TFA=5/95/0.1
Wavelength: 207 nm
Flow rate: 1 ml/min
Temperature: 40° C.

The contents of impurities and isomers were determined based on PAR (Peak Area Ratio) where the definition of PAR is as follows:

$$PAR(\%)=A/B\times100$$

wherein A means the peak area of each impurity, and B means the sum of peak areas of all the impurities except the peaks identified in the blank solution (consisting of solvent only, not the sample)

The quality standard for the impurities and isomers in terms of PAR by the present applicant company, and the results of HPLC analysis thereon are represented in the following Table 1.

TABLE 1

| | Quality Standard | Analysis result for Compound (I) prepared in Example 1 |
|---|---|---|
| E-isomer | 2.7% PAR or less | 0.96% PAR or less |
| Specific unconfirmed impurity | 1.2% PAR or less | 0.88% PAR or less |
| New impurity | 0.1% PAR or less | 0.02% PAR or less |

Further, Compounds (1), (2), (3), (4), etc. which are formed during the earlier processes for preparing Compound (I) were never detected.

All the Compounds (I) prepared according to Examples 2 to 5 also satisfied the quality standard.

INDUSTRIAL APPLICABILITY

In preparing 4-aminomethyl-3-alkoxyiminopyrrolidine methanesulfonate used as an intermediate for quinolone antibiotics, the present invention improved a couple of aspects of the previous process. Total number of steps is reduced to 2-3 steps to result in removing operations such as filtration and extractive work-up, and use of expensive reagent, (BOC)$_2$O, various organic solvents and reagents is avoided.

The invention claimed is:

1. Compound (III):

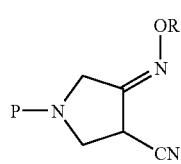

(III)

wherein R represents C$_{1-4}$ alkyl or C$_{1-4}$ haloalkyl and P represents a protecting group.

2. Compound (IV):

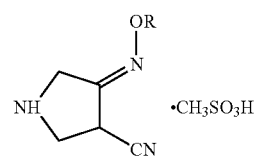

(IV)

wherein R represents C$_{1-4}$ alkyl or C$_{1-4}$ haloalkyl.

3. A process for preparing Compound (VI):

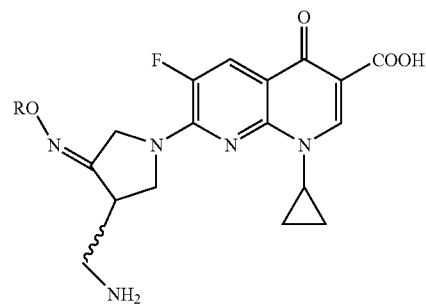

(VI)

wherein R represents C$_{1-4}$ alkyl or C$_{1-4}$ haloalkyl, which comprises the step of reacting Compound (I):

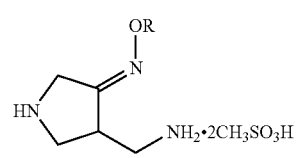

(I)

wherein R is as defined above, with Compound (V):

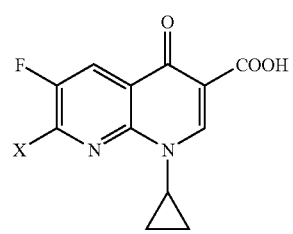

(V)

wherein X represents a leaving group; and
wherein Compound (I) is prepared by the steps of:
a) reacting Compound (II)

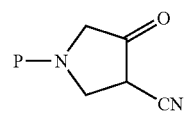

(II)

wherein P represents a protecting group, with alkoxyamine or haloalkoxyamine or salt thereof in the presence of a base to give Compound (III):

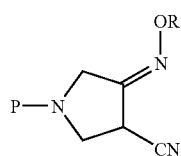
(III)

wherein R and P each are as defined above, b) reacting Compound (III) with methanesulfonic acid to give Compound (IV):

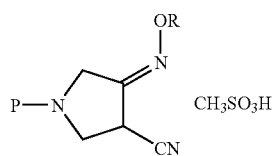
(IV)

wherein R is as defined above, and c) adding methanesulfonic acid and hydrogenation catalyst to Compound (IV) and subjecting the compound to hydrogenation reaction to give Compound (I).

4. The process of claim 3, wherein Compound (VI) is (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate or its hydrate.

5. The process of claim 3, wherein the reaction of Compound (I) with Compound (V) is carried out in the presence of a base and in a solvent.

6. The process of claim 5, wherein Compound (VI) is (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate or its hydrate.

7. A process for preparing Compound (VI):

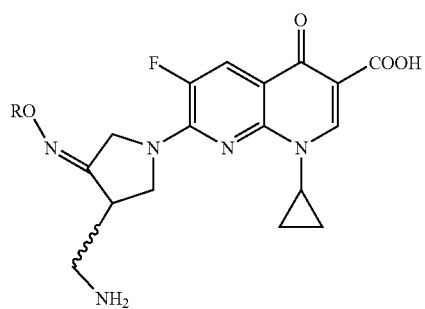
(VI)

wherein R represents $C_{1-4}$ alkyl or $C_{1-4}$ haloalkyl, which comprises the step of reacting Compound (I):

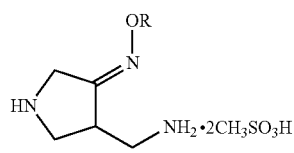
(I)

wherein R is as defined above, with Compound (V):

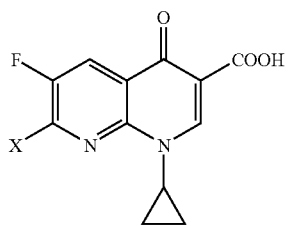
(V)

wherein X represents a leaving group; and wherein Compound (I) is prepared by the steps of:

a) reacting Compound (II):

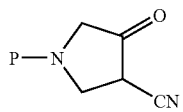
(II)

wherein P represents a protecting group, with alkoxyamine or haloalkoxyamine or a salt thereof in the presence of a base to give Compound (III):

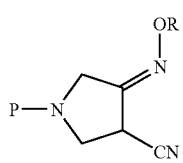
(III)

wherein R and P each are as defined above, and b) adding methanesulfonic acid and hydrogenation catalyst to Compound (III) and subjecting the compound to hydrogenation reaction to give Compound (I).

8. The process of claim 7, wherein Compound (VI) is (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate or its hydrate.

9. The process of claim 7, wherein the reaction of Compound (I) with Compound (V) is carried out in the presence of a base and in a solvent.

10. The process of claim 9, wherein Compound (VI) is (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate or its hydrate.

* * * * *